United States Patent
Matthison-Hansen et al.

(10) Patent No.: US 11,337,588 B2
(45) Date of Patent: May 24, 2022

(54) ENDOSCOPE

(71) Applicant: AMBU A/S, Ballerup (DK)

(72) Inventors: Kaspar Mat Matthison-Hansen, Helsingør (DK); Thomas Bachgaard Jensen, Copenhagen (DK); Jakob Bønnelykke Kristensen, Ølstykke (DK); Peer Hoffmann, Stenløse (DK)

(73) Assignee: AMBU A/S, Ballerup (DK)

( * ) Notice: Subject to any disclaimer, the term of this patent is extended or adjusted under 35 U.S.C. 154(b) by 221 days.

(21) Appl. No.: 16/839,991

(22) Filed: Apr. 3, 2020

(65) Prior Publication Data

US 2020/0229680 A1  Jul. 23, 2020

Related U.S. Application Data

(63) Continuation of application No. 15/576,815, filed as application No. PCT/DK2016/050152 on May 26, (Continued)

(30) Foreign Application Priority Data

| May 27, 2015 | (DK) | ............................ PA 2015 70317 |
| May 27, 2015 | (DK) | ............................ PA 2015 70318 |

(Continued)

(51) Int. Cl.
*A61B 1/00* (2006.01)
*A61B 1/005* (2006.01)
(Continued)

(52) U.S. Cl.
CPC ............ *A61B 1/0052* (2013.01); *A61B 1/008* (2013.01); *A61B 1/0055* (2013.01);
(Continued)

(58) Field of Classification Search
None
See application file for complete search history.

(56) References Cited

U.S. PATENT DOCUMENTS

| 609,370 A | 8/1898 | Sargeant |
| 609,570 A | 8/1898 | Bowden |

(Continued)

FOREIGN PATENT DOCUMENTS

| AU | 2008207558 A1 | 4/2009 |
| CN | 1125390 A | 6/1996 |

(Continued)

OTHER PUBLICATIONS

Examination report in related European application No. 16726776.4, dated Dec. 23, 220, 4 pgs.

(Continued)

*Primary Examiner* — Timothy J Neal
(74) *Attorney, Agent, or Firm* — Faegre Drinker Biddle & Reath LLP

(57) ABSTRACT

An endoscope (1) having a handle with a handle housing (2) and an insertion tube (3) extending from said handle (2) and terminating in a tip part (4) at the distal end of the endoscope (1). A working channel and having a distal end and a proximal end extends within the insertion tube (3). The endoscope further comprises motion transfer means (53, 54) extending within said working channel and adapted to operate a tool (55) at the exit port of the tip part (4) in response to the activation of an operating member (22). The working channel comprises a generally tubular working channel wall. The distal working channel end comprises an exit port at the tip part (4) at the distal end of the endoscope (1). The proximal working channel end comprises an end sealing means accommodated within the handle housing (2).

(Continued)

Figure 1:
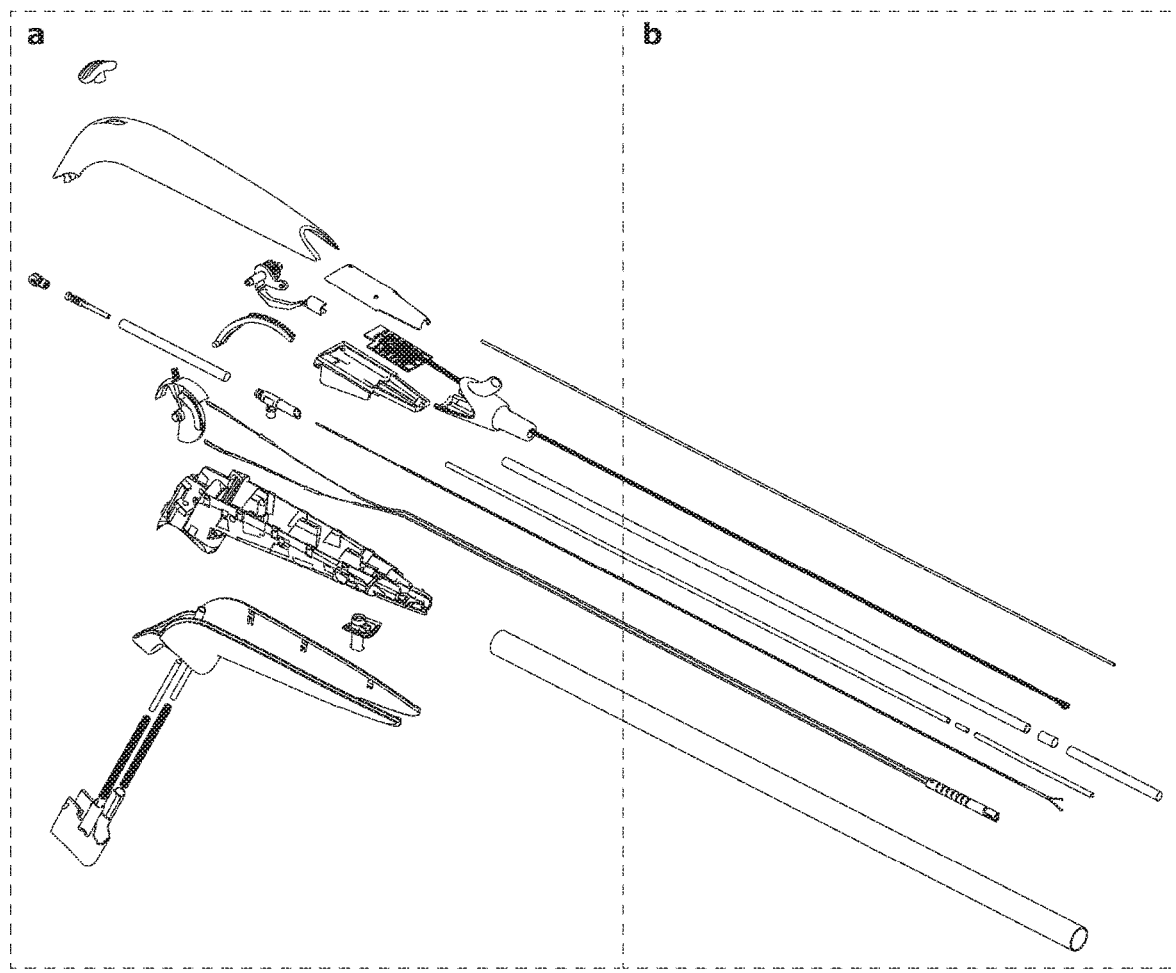

An entry port is provided between the distal working channel end and the proximal working channel end.

26 Claims, 14 Drawing Sheets

Related U.S. Application Data 2016, now Pat. No. 10,617,284, application No. 16/839,991, which is a continuation of application No. 15/576,812, filed as application No. PCT/DK2016/050154 on May 26, 2016, now Pat. No. 10,646,107, application No. 16/839,991, which is a continuation of application No. 15/576,813, filed as application No. PCT/DK2016/050149 on May 26, 2016, now Pat. No. 10,631,716, application No. 16/839,991, which is a continuation of application No. 15/576,814, filed as application No. PCT/DK2016/050153 on May 26, 2016, now Pat. No. 10,624,531, application No. 16/839,991, which is a continuation of application No. 15/576,817, filed as application No. PCT/DK2016/050151 on May 26, 2016, now Pat. No. 10,624,617.

(30)  Foreign Application Priority Data

| May 27, 2015 | (DK) | .......................... PA 2015 70320 |
| May 27, 2015 | (DK) | .......................... PA 2015 70321 |
| May 27, 2015 | (DK) | .......................... PA 2015 70322 |

(51) Int. Cl.

| *A61B 17/29* | (2006.01) |
| *A61B 1/018* | (2006.01) |
| *A61B 1/008* | (2006.01) |
| A61B 17/00 | (2006.01) |
| A61B 90/00 | (2016.01) |

(52) U.S. Cl.
CPC ...... *A61B 1/00066* (2013.01); *A61B 1/00087* (2013.01); *A61B 1/018* (2013.01); *A61B 17/29* (2013.01); *A61B 17/2909* (2013.01); *A61B 1/00045* (2013.01); *A61B 2017/003* (2013.01); *A61B 2017/0034* (2013.01); *A61B 2017/00323* (2013.01); *A61B 2017/00389* (2013.01); *A61B 2017/00424* (2013.01); *A61B 2017/2923* (2013.01); *A61B 2090/373* (2016.02)

(56)  References Cited

U.S. PATENT DOCUMENTS

| 4,203,430 | A | 5/1980 | Takahashi |
| 4,750,475 | A | 6/1988 | Yoshihashi |
| 4,757,827 | A | 7/1988 | Buchbinder et al. |
| 4,805,596 | A | 2/1989 | Hatori |
| 4,905,666 | A | 3/1990 | Fukuda |
| 5,167,221 | A | 12/1992 | Chikama |
| 5,275,151 | A | 1/1994 | Shockey et al. |
| 5,299,562 | A | 4/1994 | Heckele et al. |
| 5,373,317 | A | 12/1994 | Salvati et al. |
| 5,435,805 | A | 7/1995 | Edwards et al. |
| 5,450,851 | A | 9/1995 | Hancock |
| 5,462,527 | A | 10/1995 | Stevens-Wright et al. |
| 5,810,876 | A | 9/1998 | Kelleher |
| 5,879,289 | A | 3/1999 | Yarush et al. |
| 5,938,588 | A | 8/1999 | Grabover et al. |
| 6,007,531 | A | 12/1999 | Snoke et al. |
| 6,077,277 | A | 6/2000 | Mollenauer et al. |
| 6,258,101 | B1 | 7/2001 | Blake, III |
| 6,270,508 | B1 | 8/2001 | Klieman et al. |
| 6,390,972 | B1 | 5/2002 | Speier et al. |
| 8,790,250 | B2 | 7/2014 | Petersen et al. |
| 10,617,284 | B2 | 4/2020 | Matthison-Hansen |
| 10,624,531 | B2 | 4/2020 | Matthison-Hansen |
| 10,624,617 | B2 | 4/2020 | Matthison-Hansen et al. |
| 10,631,716 | B2 | 4/2020 | Matthison-Hansen |
| 10,645,260 | B2 | 5/2020 | Matthison-Hansen et al. |
| 10,646,107 | B2 | 5/2020 | Matthison-Hansen et al. |
| 10,779,710 | B2 | 9/2020 | Matthison-Hansen |
| 2002/0099266 | A1 | 7/2002 | Ogura et al. |
| 2003/0009176 | A1 | 1/2003 | Bilitz |
| 2005/0070764 | A1 | 3/2005 | Nobis et al. |
| 2005/0075539 | A1 | 4/2005 | Schulz et al. |
| 2005/0273085 | A1 | 12/2005 | Hinman et al. |
| 2006/0025651 | A1 | 2/2006 | Adler et al. |
| 2006/0173243 | A1 | 8/2006 | Watanabe |
| 2006/0258955 | A1 | 11/2006 | Hoffman et al. |
| 2007/0219411 | A1 | 9/2007 | Dejima et al. |
| 2007/0250038 | A1 | 10/2007 | Boulais |
| 2007/0282167 | A1 | 12/2007 | Barenboym et al. |
| 2008/0051631 | A1 | 2/2008 | Dejima et al. |
| 2008/0188868 | A1 | 8/2008 | Weitzner et al. |
| 2008/0195128 | A1 | 8/2008 | Orbay et al. |
| 2008/0249483 | A1 | 10/2008 | Slenker et al. |
| 2008/0287735 | A1 | 11/2008 | Takemoto et al. |
| 2009/0054733 | A1 | 2/2009 | Marescaux et al. |
| 2009/0076328 | A1 | 3/2009 | Root et al. |
| 2009/0209945 | A1 | 8/2009 | Lobl et al. |
| 2009/0247994 | A1 | 10/2009 | Bacher et al. |
| 2010/0022837 | A1 | 1/2010 | Ishiguro et al. |
| 2010/0030020 | A1 | 2/2010 | Sanders et al. |
| 2010/0249497 | A1 | 9/2010 | Peine et al. |
| 2010/0268268 | A1 | 10/2010 | Bacher et al. |
| 2010/0298642 | A1 | 11/2010 | Trusty et al. |
| 2011/0009694 | A1 | 1/2011 | Schultz et al. |
| 2011/0112517 | A1 | 5/2011 | Peine et al. |
| 2011/0264129 | A1 | 10/2011 | Holdgate et al. |
| 2011/0306831 | A1 | 12/2011 | Koehnke et al. |
| 2011/0306841 | A1 | 12/2011 | Lozman et al. |
| 2012/0116362 | A1 | 5/2012 | Kieturakis |
| 2014/0073855 | A1 | 3/2014 | Kindler |
| 2014/0142377 | A1 | 5/2014 | Yang et al. |
| 2014/0148759 | A1 | 5/2014 | MacNamara et al. |
| 2014/0206936 | A1 | 7/2014 | Cooper et al. |
| 2014/0221749 | A1 | 8/2014 | Grant et al. |
| 2014/0243615 | A1 | 8/2014 | Schaeffer et al. |
| 2014/0275763 | A1 | 9/2014 | King et al. |
| 2014/0316203 | A1 | 10/2014 | Carroux et al. |
| 2014/0336532 | A1 | 11/2014 | Seguy |
| 2015/0282701 | A1 | 10/2015 | Oskin et al. |
| 2015/0366436 | A1 | 12/2015 | Iuel |
| 2016/0095585 | A1 | 4/2016 | Zergiebel et al. |
| 2016/0150946 | A1 | 6/2016 | Tsumaru et al. |
| 2016/0348769 | A1 | 12/2016 | Siegal |
| 2018/0203316 | A1 | 7/2018 | Xu |
| 2018/0203317 | A1 | 7/2018 | Li et al. |
| 2018/0296068 | A1 | 10/2018 | Matthison-Hansen et al. |
| 2018/0296069 | A1 | 10/2018 | Matthison-Hansen |
| 2018/0303315 | A1 | 10/2018 | Matthison-Hansen |
| 2018/0303316 | A1 | 10/2018 | Matthison-Hansen |
| 2018/0303317 | A1 | 10/2018 | Matthison-Hansen |
| 2018/0303472 | A1 | 10/2018 | Matthison-Hansen et al. |
| 2018/0309908 | A1 | 10/2018 | Matthison-Hansen et al. |
| 2020/0267292 | A1 | 8/2020 | Matthison-Hansen et al. |
| 2020/0352413 | A1 | 11/2020 | Matthison-Hansen et al. |

FOREIGN PATENT DOCUMENTS

| CN | 1956684 A | 5/2007 |
| CN | 101513338 A | 8/2009 |
| CN | 102871636 A | 1/2013 |
| CN | 103505176 A | 1/2014 |
| CN | 203506676 U | 4/2014 |
| CN | 203885470 U | 10/2014 |
| CN | 204120980 U | 1/2015 |
| EP | 0567146 A2 | 10/1993 |
| EP | 1484003 A1 | 12/2004 |
| EP | 1561413 A1 | 8/2005 |
| JP | 09-010166 A | 1/1997 |

(56) References Cited

FOREIGN PATENT DOCUMENTS

| WO | 2005/112806 A2 | 12/2005 |
|---|---|---|
| WO | 2008/033356 A2 | 3/2008 |
| WO | 2008/045374 A2 | 4/2008 |
| WO | 2008/061106 A1 | 5/2008 |
| WO | 2010/066789 A1 | 6/2010 |
| WO | 2010/066790 A1 | 6/2010 |
| WO | 2013/071938 A1 | 5/2013 |
| WO | 2013/106444 A1 | 7/2013 |
| WO | 2014/127780 A1 | 8/2014 |

OTHER PUBLICATIONS

International Search Report for PCT/DK2016/050150 dated Aug. 11, 2016, 5 pages.
Article 94(3) EPC communication in related EP appl. No. 16726781. 4, dated Oct. 26, 2018; 5 pgs.
Danish Patent and Trademark Office Action for Appl No. PA201570321 dated Sep. 3, 2015, 3 pages.
Danish Patent and Trademark Office Search Report for Appl No. PA201570317 dated Aug. 25, 2015, 6 pages.
Danish Patent and Trademark Office Search Report for Appl No. PA201570318 dated Aug. 27, 2015, 4 pages.
Danish Patent and Trademark Office Search Report for Appl No. PA201570319 dated Aug. 31, 2015, 9 pages.
Danish Patent and Trademark Office Search Report for Appl No. PA201570320 dated Oct. 21, 2015, 7 pages.
Danish Patent and Trademark Office Search Report for Appl No. PA201570321 dated Sep. 2, 2015, 2 pages.
Danish Patent and Trademark Office Search Report for Appl No. PA201570322 dated Aug. 25, 2015, 7 pages.
Danish Patent and Trademark Office Search Report for Appl No. PA201570323 dated Jul. 9, 2015, 8 pages.
EPC communication in related EP appl. No. 16 726 Ih A, dated Sep. 25, 2018; 2 pgs.
Examination report in related Chinese application No. 2016800384403, dated Dec. 28, 2018, 11 pgs.
Examination report in related Chinese application No. 201680038859.9 dated Aug. 2, 2019, 9 pgs.
Examination report in related Chinese application No. 2016800388599 dated Dec. 28, 2018, 9 pgs.
Examination report in related Chinese application No. 201680038906X dated Nov. 26, 2018, 6 pgs.
Examination report in related Chinese application No. 2016800390616, dated Dec. 28, 2018, 9 pgs.
Examination report in related Chinese application No. 2016800390902 dated Dec. 11, 2018, 9 pgs.
Examination report in related Chinese application No. 2016800390902 dated Jul. 15, 2019, 4 pgs., including summary translation from Chinese counsel.
Examination report in related Chinese application No. 201680039147. 9, dated Dec. 28, 2018 and translation from examiner.
Examination report in related Chinese application No. CN201680036584.5, dated Nov. 12, 2018; 8 pgs.
International Preliminary Report on Patentability received for PCT Patent Application No. PCT/DK2016/050148, dated Dec. 7, 2017, 7 pages.
International Preliminary Report on Patentability received for PCT Patent Application No. PCT/DK2016/050149, dated Dec. 7, 2017, 7 pages.
International Preliminary Report on Patentability received for PCT Patent Application No. PCT/DK2016/050150, dated Dec. 7, 2017, 7 pages.
International Preliminary Reporton Patentability received for PCT Patent Application No. PCT/DK2016/050151, dated Dec. 7, 2017, 8 pages.
International Preliminary Reporton Patentability received for PCT Patent Application No. PCT/DK2016/050153, dated Dec. 7, 2017, 9 pages.
International Preliminary Report on Patentability received for PCT Patent Application No. PCT/DK2016/050154, dated Dec. 7, 2017, 8 pages.
International Search Report for PCT/DK2016/050148 dated Aug. 11, 2016, 5 pages.
International Search Report for PCT/DK2016/050150 dated Aug. 1, 2016, 5 pages.
International Search Report for PCT/DK2016/050151 dated Aug. 9, 2016, 5 pages.
International Search Report for PCT/DK2016/050152 dated Aug. 5, 2016, 5 pages.
International Search Report for PCT/DK2016/050153 dated Aug. 9, 2016, 4 pages.
International Search Report issued in PCT/DK2016050149, dated Aug. 5, 2016, 4 pages.
International Search Report issued in PCT/DK2016050154, dated Aug. 8, 2016, 7 pages.
Office Action dated Jan. 13, 2020 in Chinese application No. 201680036584.5 with translation of content.
Office Action in corresponding Chinese application No. 201680036584 dated Jul. 22, 2019, 5 pgs., including summary translation from Chinese counsel.
Office Action in corresponding Chinese application No. 201680039061 dated Aug. 2, 2019, 6 pgs., including summary translation from Chinese counsel.
Office Action in corresponding Chinese application No. 20168003914 7 dated Aug. 2, 2019, 9 pgs., including summary translation from Chinese counsel.
Search Report issued by the Chinese Patent Office, dated Mar. 3, 2020, for related Chinese Patent Application No. 201680038859.9; 9 pages.
Search Report issued by the Chinese Patent Office, dated Mar. 3, 2020, for related Chinese Patent Application No. 201680039061.6; 10 pages.
Search Report issued by the European Patent Office, dated Jun. 17, 2020 for related Application No. 16 726 778.0; 5 pages.
Written Opinion ISA for PCT/DK2016/050148 dated Aug. 10, 2016 in European Register, 46 pages.
Written Opinion of the International Searching Authority for PCT/DK2016/050149 dated Aug. 4, 2016 in European Register, 5 pages.
Written Opinion of the International Searching Authority for PCT/DK2016/050150 dated Aug. 10, 2016 in European Register, 5 pages.
Written Opinion of the International Searching Authority for PCT/DK2016/050151 dated Aug. 8, 2016 in European Register, 6 pages.
Written Opinion of the International Searching Authority for PCT/DK2016/050152 dated Aug. 4, 2016 in European Register, 6 pages.
Written Opinion of the International Searching Authority for PCT/DK2016/050153 dated Aug. 8, 2016 in European Register, 7 pages.
Written Opinion of the International Searching Authority for PCT/DK2016/050154 dated Aug. 4, 2016 in European Register, 6 pages.

ENDOSCOPE

CROSS-REFERENCE TO RELATED APPLICATIONS

This is a continuation of U.S. patent application Ser. No. 15/576,815 and U.S. patent application Ser. Nos. 15/576,812, 15/576,813, 15/576,814, and 15/576,817, all filed Nov. 25, 2017. U.S. patent application Ser. No. 15/576,815 is a § 371 filing of International Appl. No. PCT/DK2016/050152, filed May 26, 2016, which claims priority to Denmark Patent Appl. No. PA 2015 70320, filed May 27, 2015. U.S. patent application Ser. No. 15/576,812 is a § 371 filing of International Appl. No. PCT/DK2016/050154, filed May 26, 2016, which claims priority to Denmark Patent Appl. No. PA 2015 70322, filed May 27, 2015. U.S. patent application Ser. No. 15/576,813 is a § 371 filing of International Appl. No. PCT/DK2016/050149, filed May 26, 2016, which claims priority to Denmark Patent Appl. No. PA 2015 70318, filed May 27, 2015. U.S. patent application Ser. No. 15/576,814 is a § 371 filing of International Appl. No. PCT/DK2016/050153, filed May 26, 2016, which claims priority to Denmark Patent Appl. No. PA 2015 70321, filed May 27, 2015. U.S. patent application Ser. No. 15/576,817 is a § 371 filing of International Appl. No. PCT/DK2016/050151, filed May 26, 2016, which claims priority to Denmark Patent Appl. No. PA 2015 70317, filed May 27, 2015. All the applications listed above are commonly owned and are incorporated herein by reference in their entirety.

The present invention relates to an endoscope, in particular but not exclusively a disposable camera endoscope, having an operating handle arranged at a proximal end thereof and an insertion tube extending from said handle towards a distal end of the endoscope.

In general an endoscope comprises an operating handle at the proximal end and an insertion tube extending from the handle towards the distal end. The handle is adapted to be held by an operator and inter alia comprises externally protruding operating members connected to internal control means allowing the operator to control the movement of a bending section at the distal end of the insertion tube, while advancing the distal end of the insertion tube to a desired location e.g. within a body cavity of a person. By means of an attached monitoring device, such as a monitor with a display screen, the location to which the distal end has been advanced may be inspected using the endoscope. Often, however, inspection is not all that is desired, e.g. where the inspection is to locate the site for further actions. One such action could be the removal of an implanted stent, which necessitates the use of a tool.

In this respect WO2013/071938A1 discloses an endoscope with a built in tool in the form of a hook adapted to grip e.g. an urological stent, which can then be removed by retracting the endoscope. The endoscope is adapted for single handed use by an operator using the thumb to control the movement of the distal tip of the endoscope, and the index finger to control the reciprocating motion of the tool. The built in tool, however, does not allow other actions than gripping. The tool is controlled in a separate channel as compared to the working channel, through which fluid may be extracted or infused. Moreover, the full activation of the tool requires a reciprocating motion both out and in of the tip part of the bending section of the insertion tube of the endoscope. Given that stereoscopic vision is not available because only a single camera is used, it may be difficult for an operator to efficiently complete this reciprocating motion in a correct manner.

US2005/0070464 discloses an accessory to an endoscope. In conjunction with this accessory for an endoscope, a number of different tools for the accessory are disclosed. The accessory is not itself an endoscope as it comprises neither camera and illumination means, or similar, nor means for controlling the movement of the distal end. Instead it is adapted to be inserted through a working channel of the endoscope. The accessory is adapted for single handed use, and could in principle be used with the endoscope of WO2013/071938A1 by insertion through the working channel were a second or alternative tool to be used.

The tool of the accessory disclosed in US2005/0070464A could in principle also be used in conjunction with the endoscope disclosed in U.S. Pat. No. 5,275,151A which has a working channel with two entry ports. One entry port is axially arranged and adapted for the insertion of a laser fibre or other tool. The other entry port is lateral and joins the other in a Y-junction of the working channel within the handle of the endoscope. The other entry port is adapted for entry of flushing fluid. However, similar to WO2013/071938A1 the operating means allows only the advancing and retracting of the tool. Moreover, the endoscope of U.S. Pat. No. 5,275,151A is not adapted for single hand use. One hand is required for the control of the advancing and retracting of the tool, whereas a second hand is needed to control the motion of the bending section of at the tip at the distal end of the insertion tube. Using the accessory of US2005/0070464A with the endoscope of U.S. Pat. No. 5,275,151A would thus require a third hand.

Moreover, even though, having the tool located in a separate working channel, as compared to the working channel, through which fluid may be extracted or infused, it provides drawbacks in other senses, in particular the extra channel takes up space within the insertion tube, where the available space is already.

Based on this prior art it is the object of the present invention to provide an endoscope with a movable tool and a working channel for extraction or infusion of fluid, and having an improved utilization of the space available within the insertion tube of the endoscope.

In this respect the present invention suggest to accommodate the movable parts, in particular the motion transfer members within the same working channel as is used for extracting of infusing fluids.

However, accommodating the movable parts within the same working channel as is used for fluids is provides new problems, because sealing around movable parts is inherently difficult.

Consequently, it is a particular object of the present invention to provide an endoscope with a movable tool and a working channel for extraction or infusion of fluid and having good sealing properties, as well as a good utilization of the space available within the endoscope.

According to a first aspect of the invention this is achieve by an endoscope having a handle with a handle housing arranged at a proximal end of the endoscope and an insertion tube extending from said handle and terminating in a tip part at the distal end of the endoscope, and a working channel extending within said insertion tube and having distal end and a proximal end, said endoscope further comprising motion transfer means extending within said working channel and adapted to operate a tool at the exit port of the tip part in response to the activation of an operating member, characterized in that the working channel comprises a generally tubular working channel wall, the distal working channel end comprises an exit port at the tip part at the distal end of the endoscope, the proximal working channel end comprises an end sealing means accommodated within the handle housing, and an entry port is provided between the distal working channel end and the proximal working channel end.

With this configuration it becomes possible to provide a part of the generally tubular working channel in a way that provides large freedom in the design of the kinematic chains between the operating member and motion transfer members and, in turn, the tool to be activated. At the same time this is done in a way which obviates the need for breaching the integrity of the working channel wall and the termination thereof at the proximal end.

According to a preferred embodiment according to the first aspect of the invention, the motion transfer means comprises a first motion transfer member and a second motion transfer member movable relatively to each other and relatively to at least a part of the working channel within said working channel. Such a configuration efficiently utilises the possibilities of the aforementioned configuration, while at the same time preserves the unbreached integrity of the working channel.

According to a further preferred embodiment according to the first aspect of the invention, the first motion transfer member is rigidly attached to the end sealing means. In this way the integrity of the working channel remains unbreached, and efficiently allows the provision of a first kinematic chain between the operating member and the first motion transfer member, where the sealing end means forms part of the kinematic chain.

This is in particular the case when, according to an especially preferred embodiment of the first aspect of the invention, the a least one part of the working channel wall is adapted to vary in length in response to movement of said sealing end means.

According to a further preferred embodiment of the first aspect of the invention, the least one part of the working channel wall comprises a hose part which is more flexible than the remainder of the working channel wall. This also allows the at least one part of the working channel wall to flex and curve in other directions, so as to accommodate different lay-outs of the kinematic chains.

According to another preferred embodiment, the working channel comprises a bifurcated section providing the entry port, the at least one part of the working channel being located between the bifurcated section and the sealing end means. Thereby it becomes very easy to attach and seal the hose part and it is ensured that the deformations of the flexible working channel wall of the hose part does not adversely influence the flow of fluid in the remainder of the working channel.

According to yet another preferred embodiment, a second kinematic chain is provided between the operating member and the second motion transfer member, said at least one part of the working channel wall forming part of said kinematic chain. Simply using the working channel wall itself as an intermediate part of the kinematic chain is an efficient way of avoiding any breach of the integrity thereof.

This is in particular the case when, according to a further preferred embodiment, the second kinematic chain comprises a clamping member, clamping the at least one part of the working channel wall between an engagement member and the clamping member. Thereby assembly is facilitated.

According to a further preferred embodiment, one and/or both of said engagement member and said clamping member is adapted to ensure an open working channel all the way to the sealing end means. Thereby, it is ensured that the working channel is accessible for ETO sterilization after assembly, which in turn is important because the endoscope is preferably a disposable endoscope made at least partially from materials not capable of withstanding autoclaving.

According to a second aspect of the invention there is provided a system comprising a monitoring device and an endoscope as described above adapted to be mutually connected to each other.

Figure 1A:
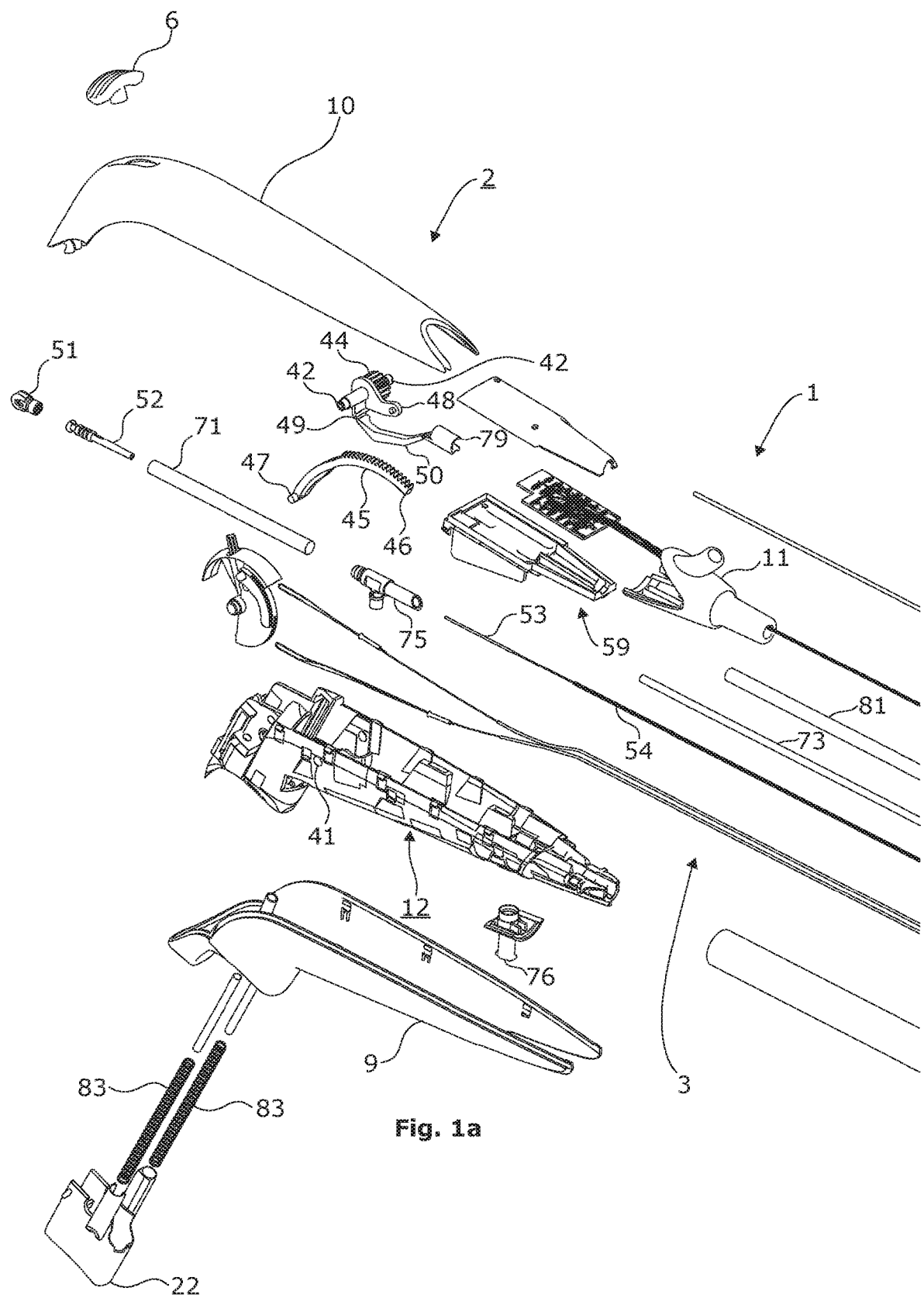
Figure 1B:
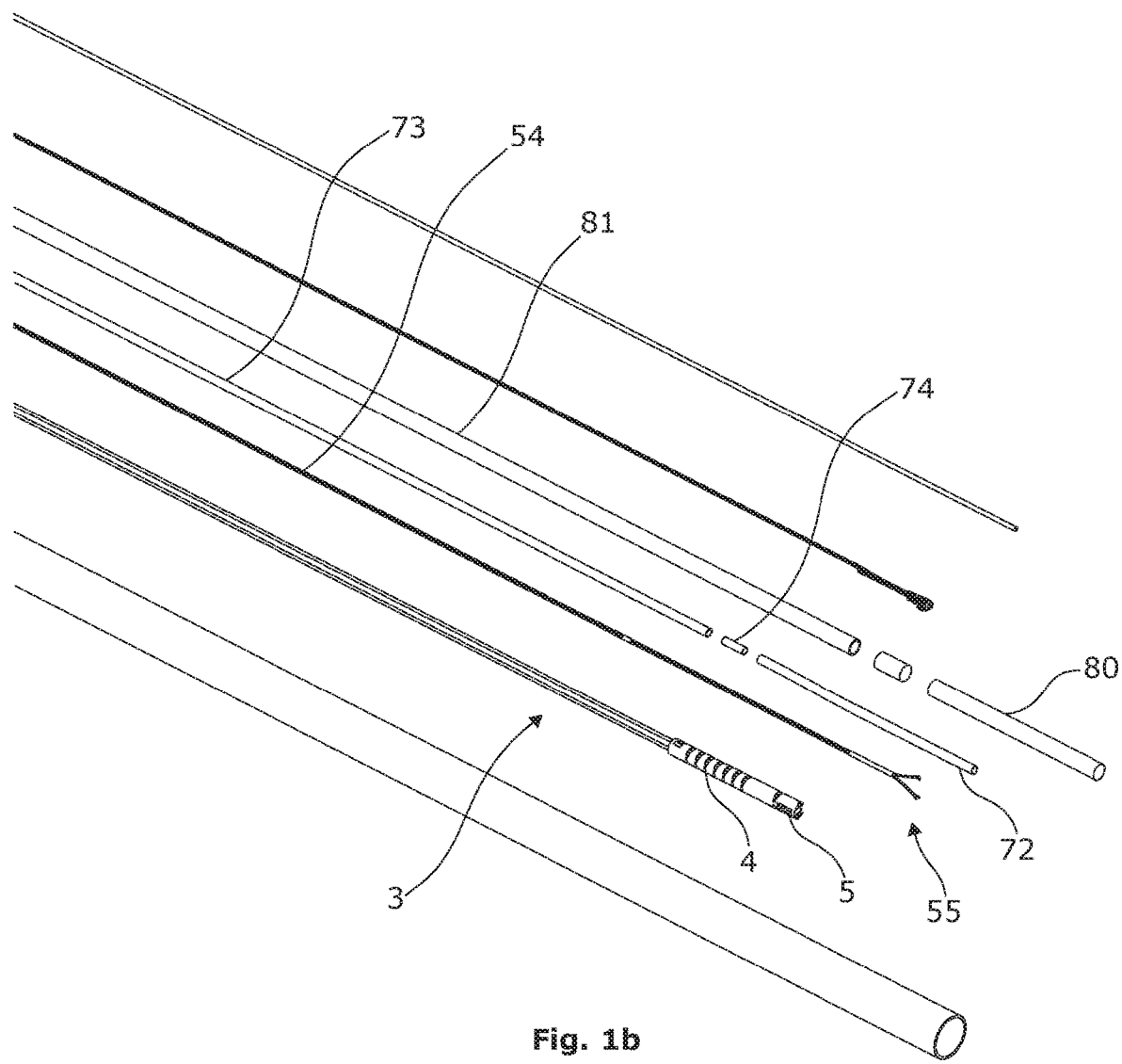
Figure 2:
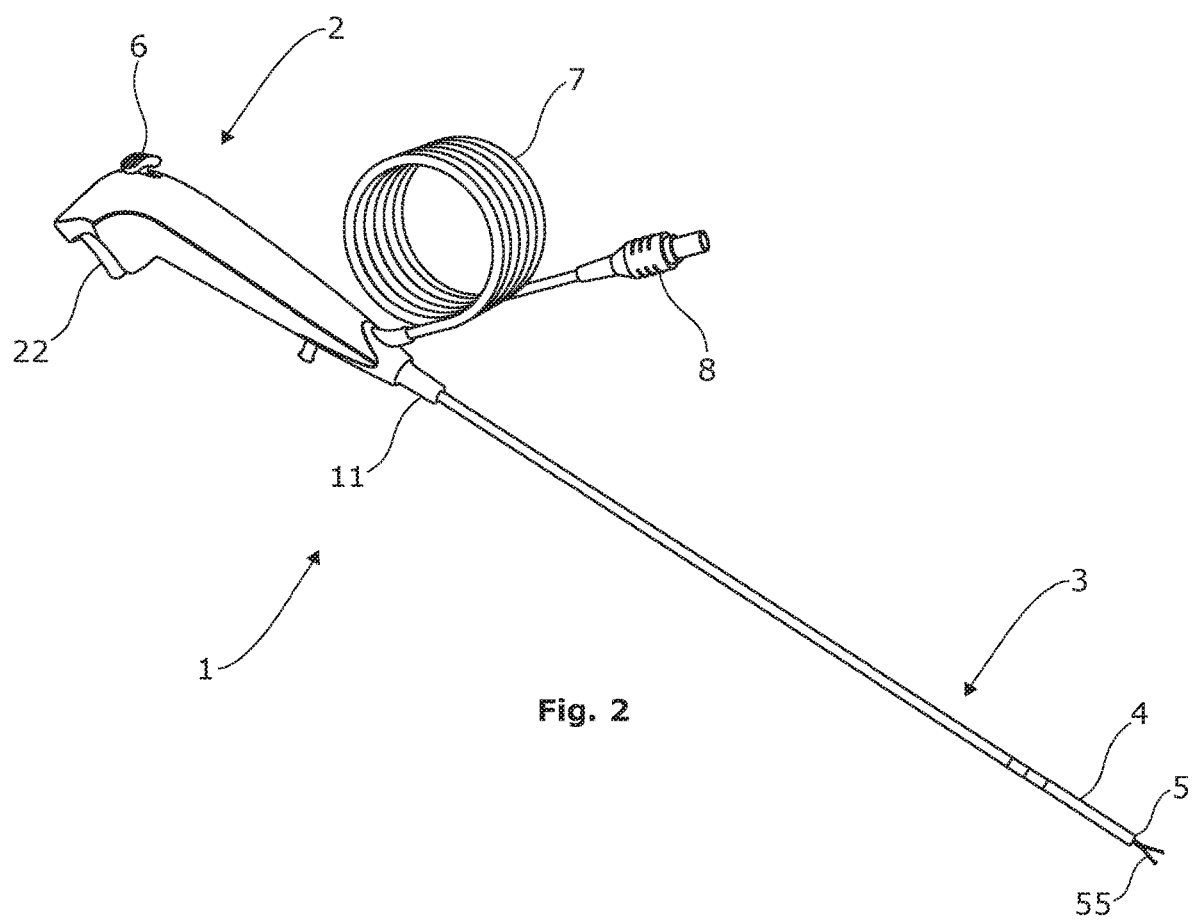
Figure 3:
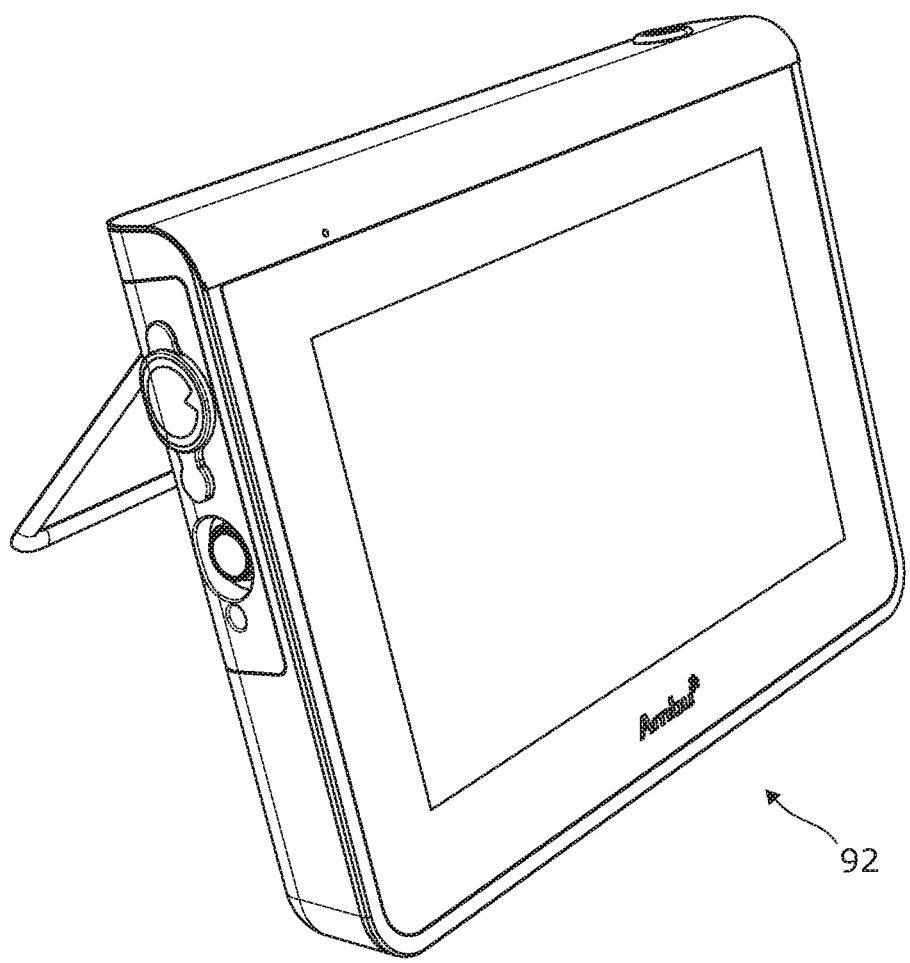
Figure 4A:
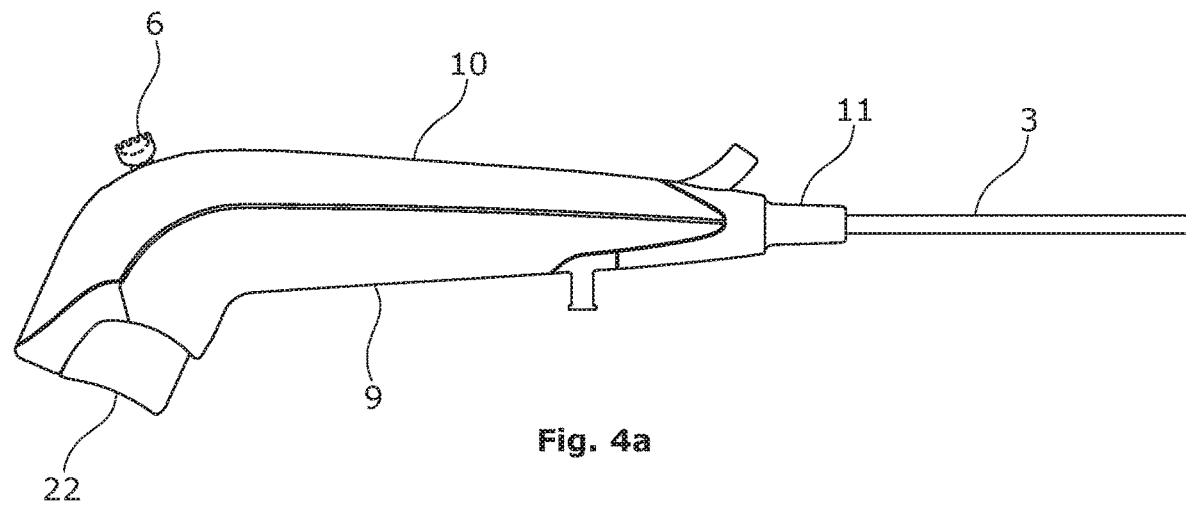
Figure 4B:
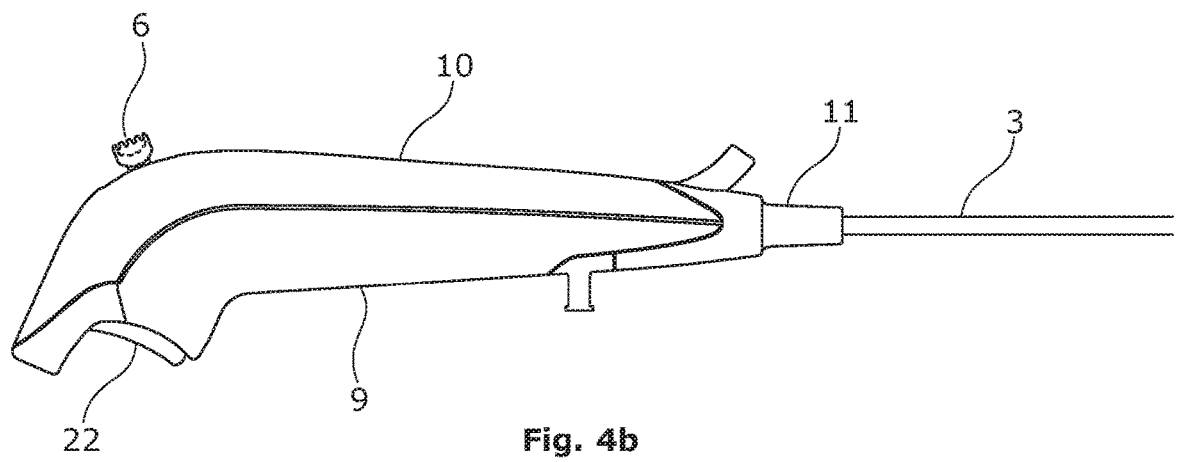
Figure 5:
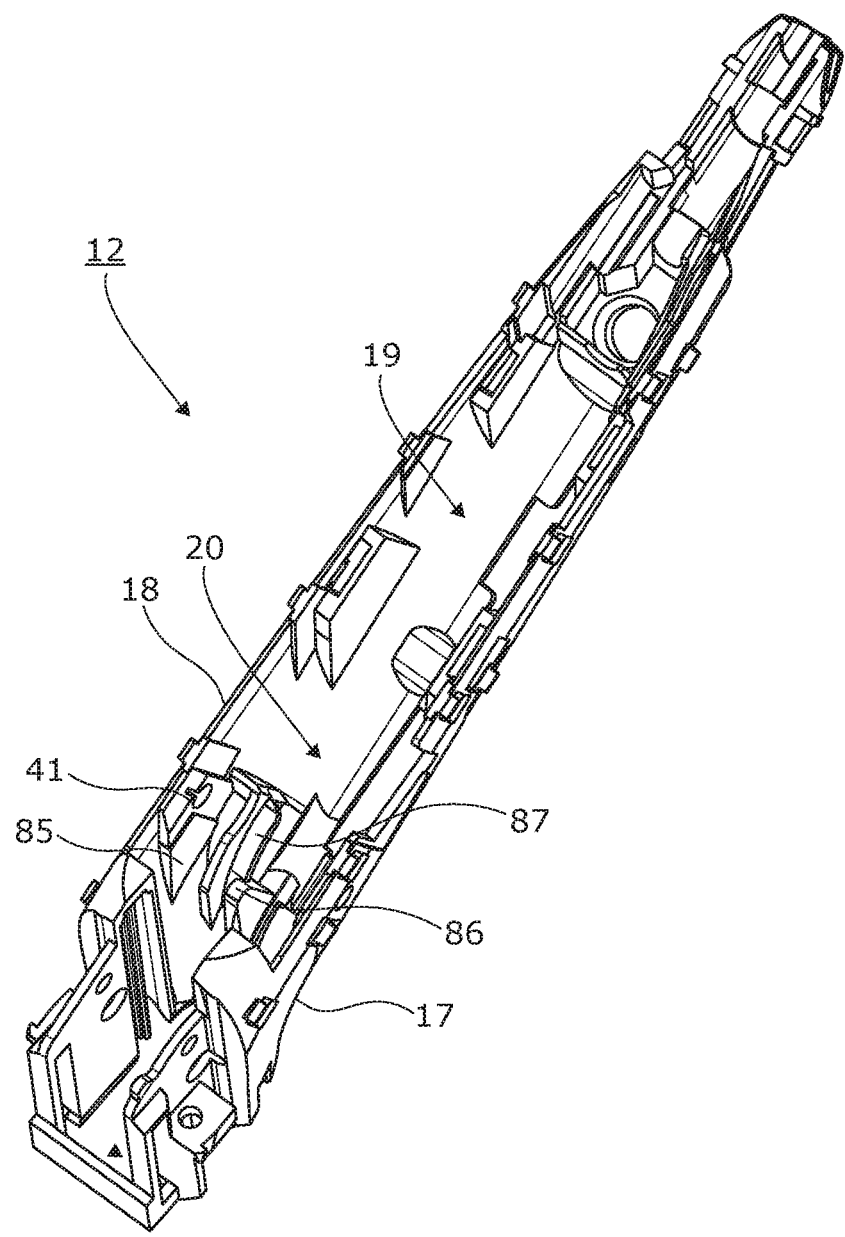
Figure 6:
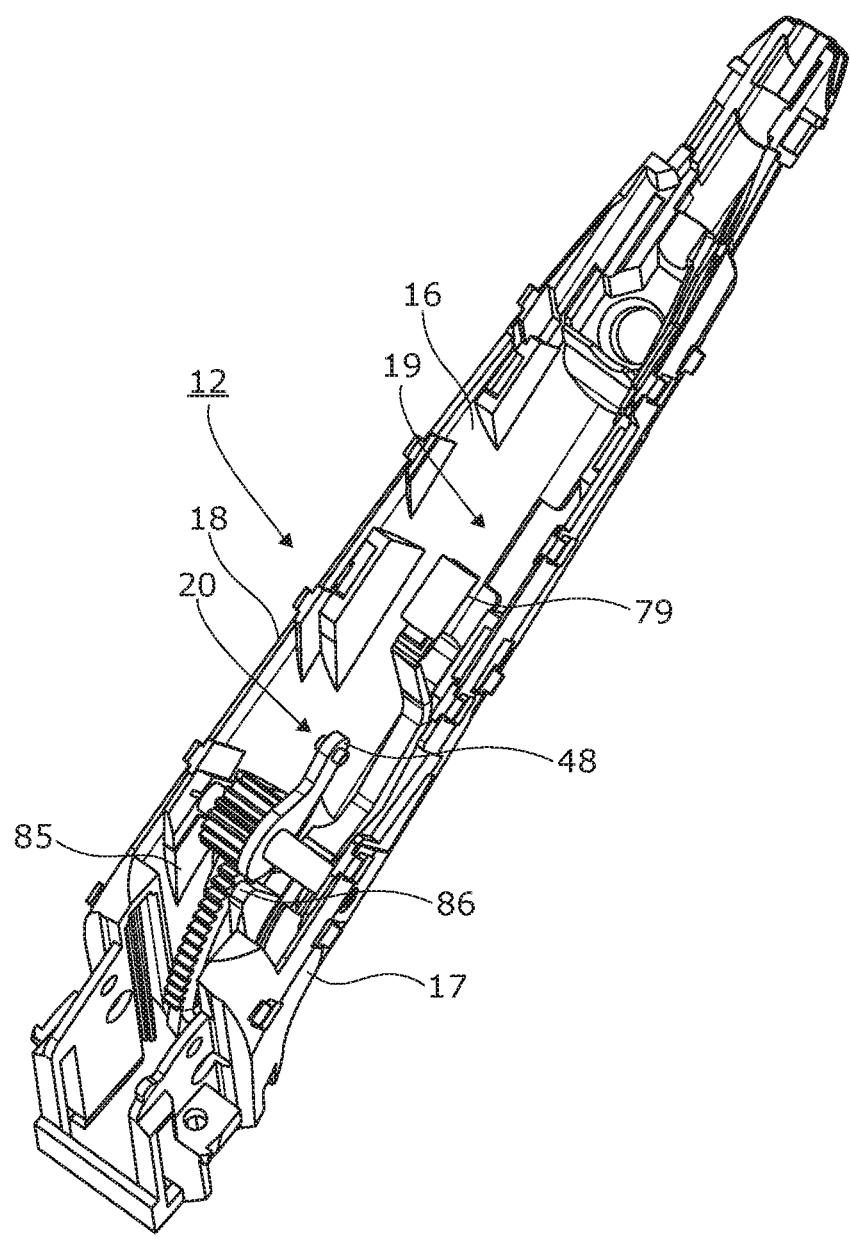
Figure 7:
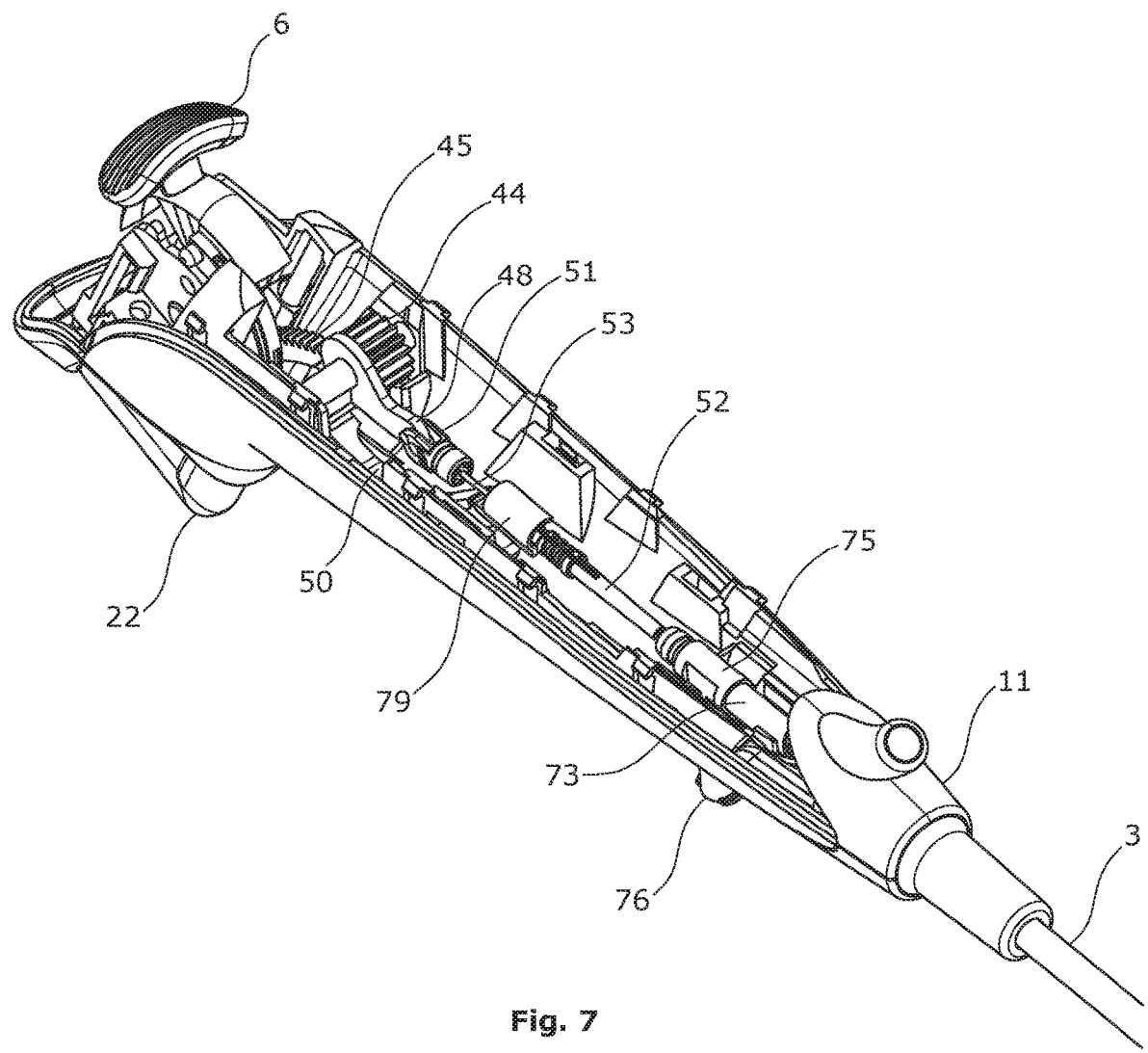
Figure 8:
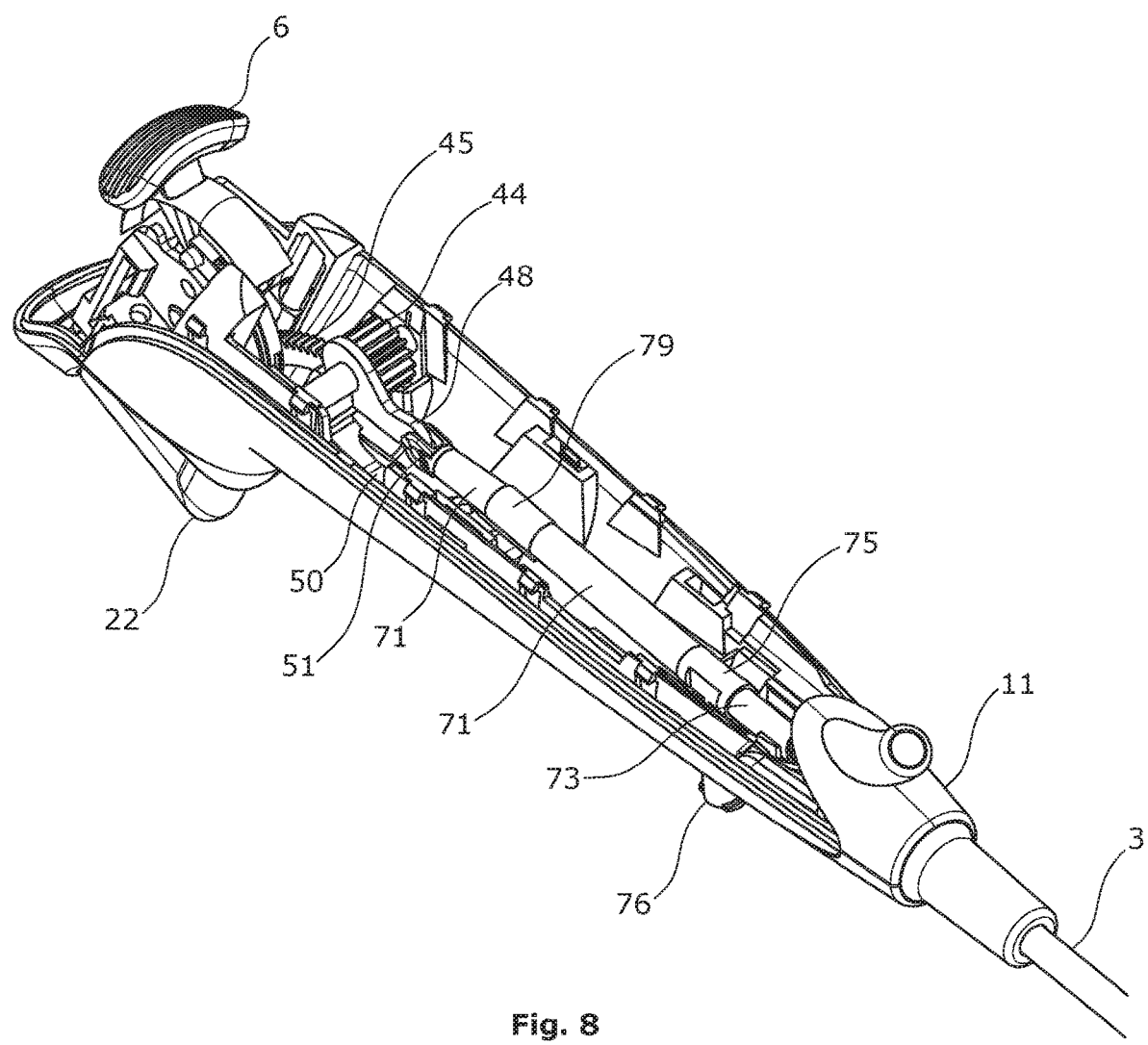
Figure 9:
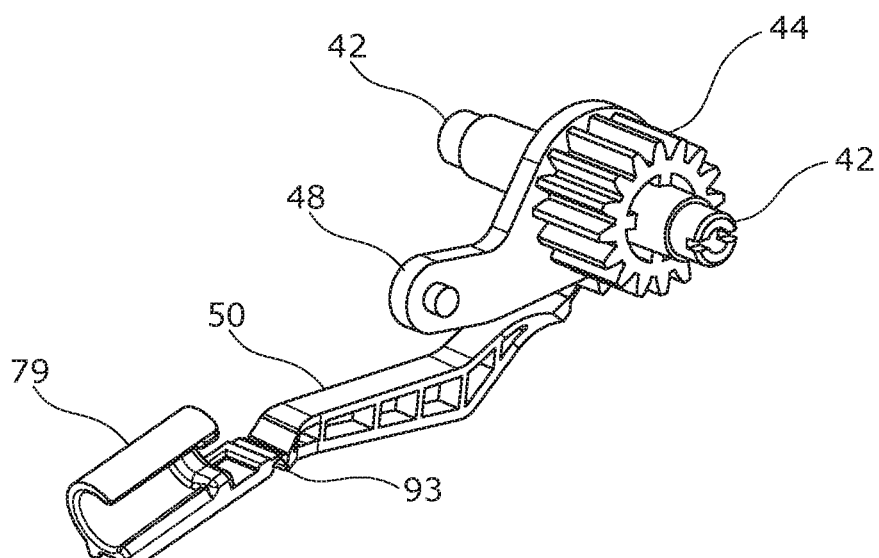
Figure 10:
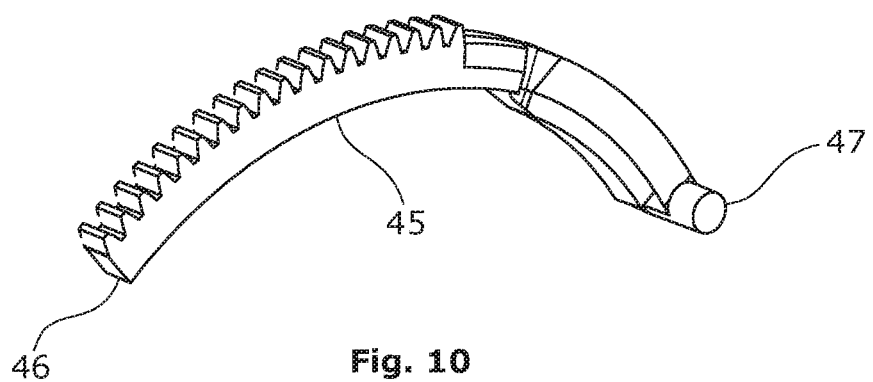
Figure 11:
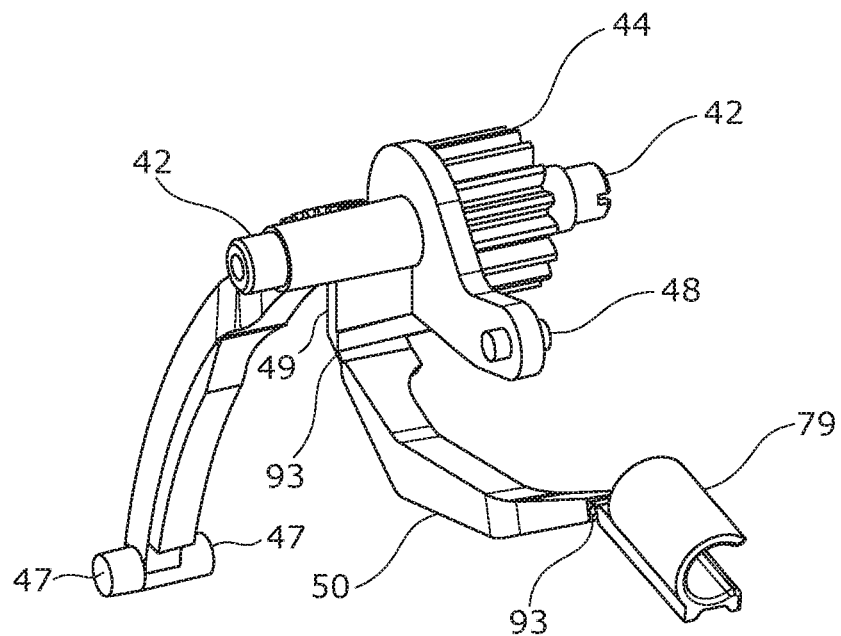
Figure 12:
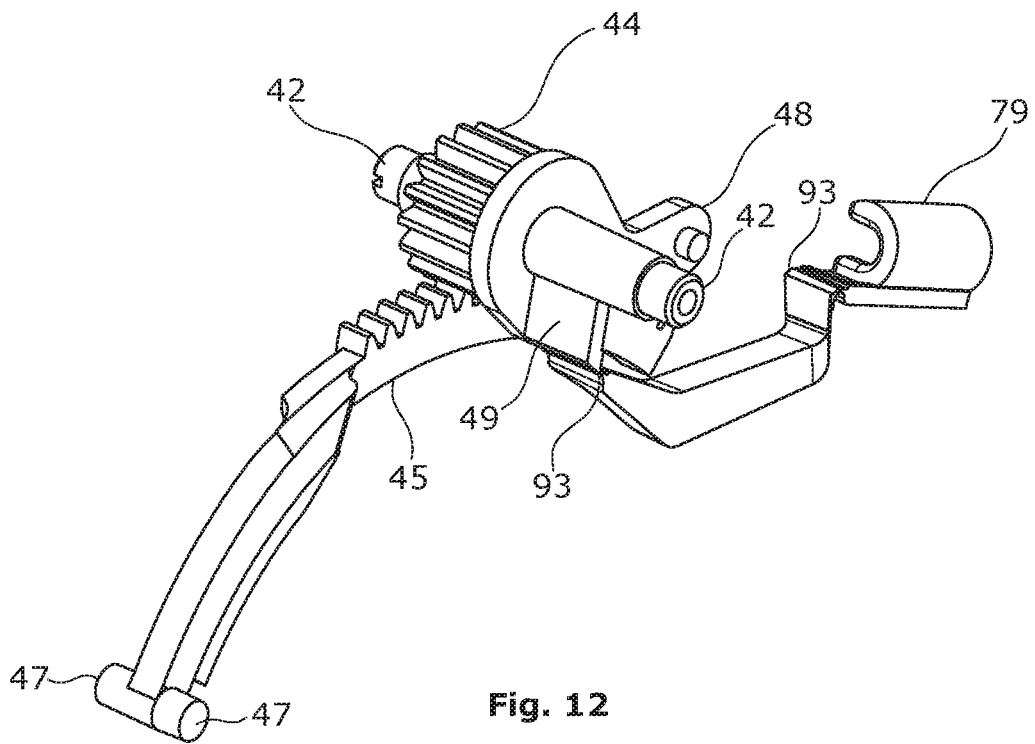
Figure 13:
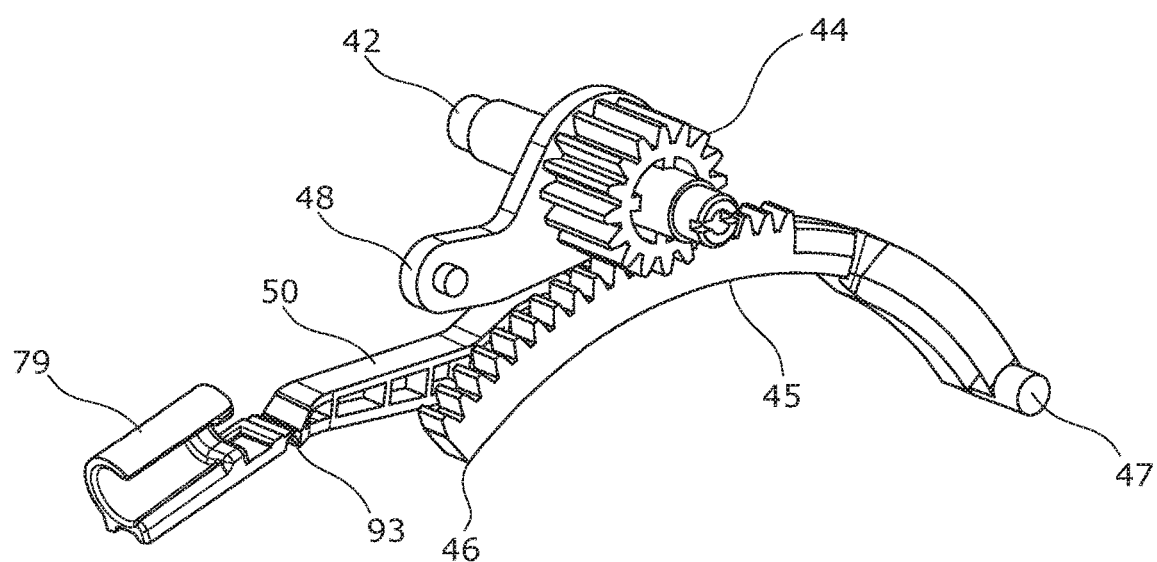
Figure 14:
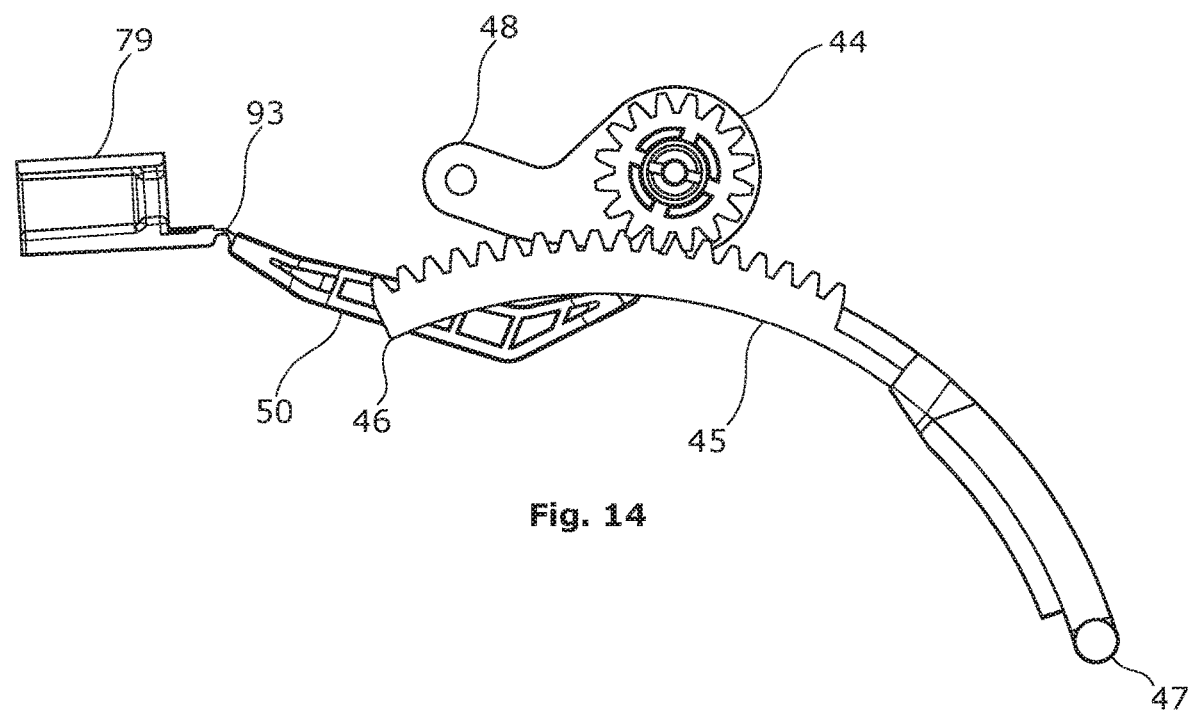
Figures 15A, 15B, 15C:
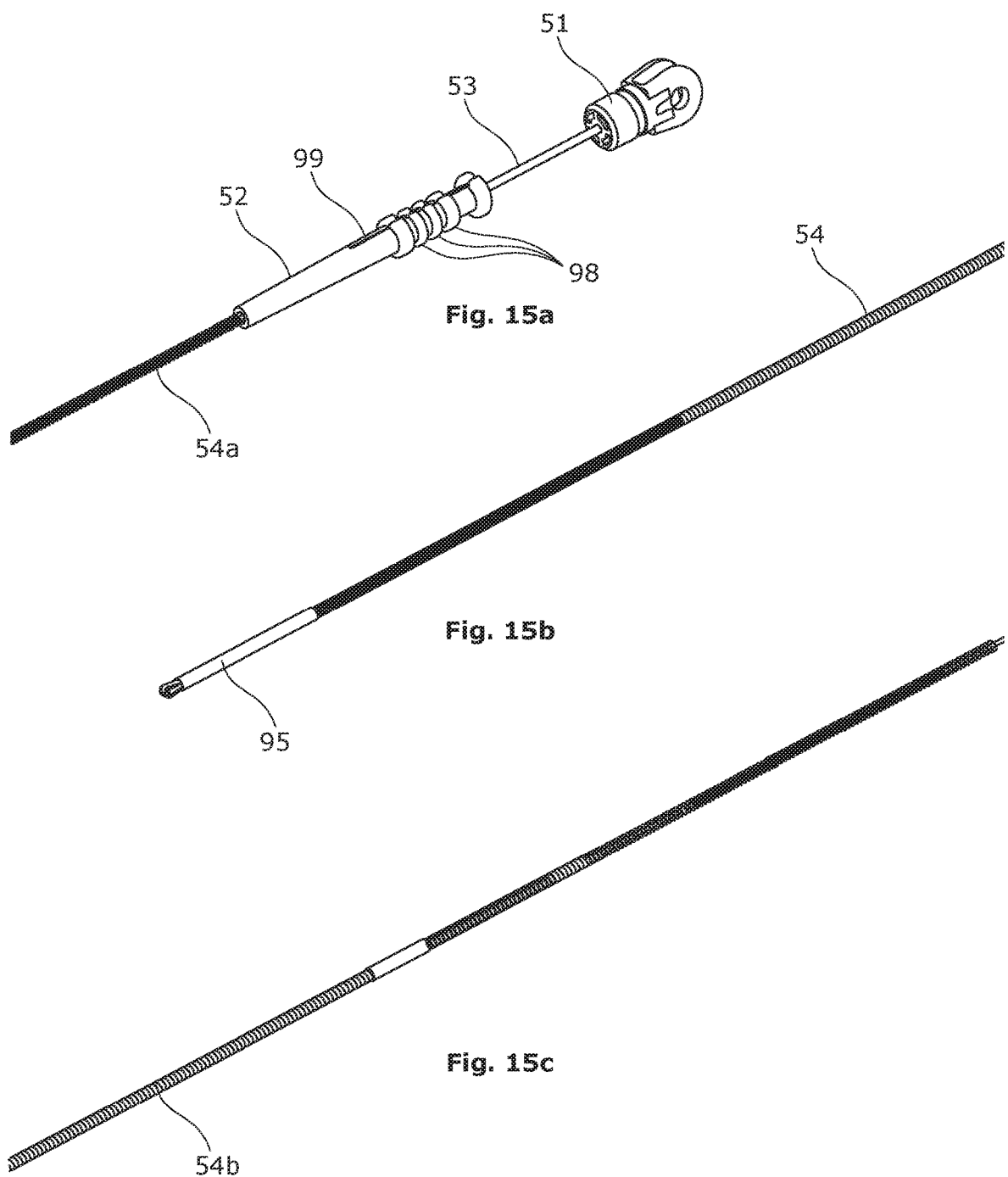

The invention will now be described in greater detail based on non-limiting exemplary embodiment and the drawing on which:

FIG. 1 shows an exploded overview of an endoscope according to the present invention and how this exploded view is split in a left-hand side part and a right-hand side part for better visibility in FIGS. 1a and 1b, FIG. 2 shows a perspective view of the fully assembled endoscope of FIG. 1, FIG. 3 shows a monitoring device for mutual connection with the endoscope of FIG. 1, FIG. 4a and FIG. 4b show partial views of the endoscope of FIG. 1 with the tool operating member in released and depressed state, respectively, FIG. 5 shows show an internal chassis of the endoscope, FIG. 6 shows the chassis of FIG. 5 with a rack and pinion mounted, FIG. 7 shows the chassis of FIG. 6 partially mounted in the handle housing partially mounted in the handle housing and with rack and pinion of FIG. 6 attached to a motion transfer means, FIG. 8 corresponds to FIG. 7 but with the motion transfer means enclosed in a part of the working channel of the endoscope, FIG. 9 shows a first perspective view of the pinion of FIG. 6, FIG. 10 shows a perspective view of the rack of FIG. 6, FIG. 11 shows a second perspective view of the pinion of FIG. 6, FIG. 12 shows a first perspective view of the rack and pinion of FIG. 6 in mutual engagement, FIG. 13 shows a second perspective view of the rack and pinion of FIG. 6 in mutual engagement, FIG. 14 shows a plan view of the rack and pinion of FIG. 6 in mutual engagement, and FIGS. 15a-c show different sectors of motion transfer means comprising a first motion transfer member and a second motion transfer member.

Turning first to FIG. 2 an assembled endoscope 1 according to the present invention is shown. The endoscope 1 has a proximal end with an operating handle 2 to be held in one hand by an operator. Accordingly, the operating handle is shaped in a manner ergonomically suitable for operator, in particular but not exclusively for the hand of the operator, as arms and joints may also play a role in the ergonomics. From the handle 2 an insertion tube 3 extends towards the distal end of the endoscope. At the distal end of the endoscope 1 the insertion tube 3 ends in a bending section 4 and a tip part 5. The bending section 4 is in mechanical connection with a first operating member 6, digitally operable by the operator, e.g. by the thumb, thereby allowing the operator to bend the tip part 5 in a desired direction when advancing the insertion tube 3 towards a desired location, e.g. through a body cavity of a patient. In addition to the first operating member 6 the endoscope 1 comprises a tool operating member 22 adapted to operate a tool 55 at the tip part 5 of the endoscope 1 handle comprises. The tool operating member 22 is preferably in the form of a trigger or pushbutton so accommodated in the housing that it may be operated by the same hand as used for operating first operating member 6. In the configuration shown the first operating member 6 is adapted to be operated by the thumb of the operator whereas the push-button is adapted to be depressed independently thereof by the index finger of the very same hand of the operator. This allows singled handed use of the endoscope. As can be seen the push-button has been partially depressed allowing the tool 55 to be advanced forwardly from the distal end of the tip 5 of the endoscope 1. This partially depressed position which will be described in greater detail later is an intermediate position between the fully released position shown in FIG. 4*a*, towards which the push-button is preferably spring biased, and the fully depressed position shown in FIG. 4*b*, which will also be described later.

As can also be seen in FIG. 2, the endoscope 1 comprises a flexible connection cable 7 with a connector 8 allowing the endoscope 1 to be connected to a monitoring device such as a monitor 92 shown in FIG. 3 forming part of an endoscope 1 and monitor 92 system.

Turning now to FIGS. 1, 1*a* and 1*b* an exploded view of the endoscope 1 is shown. As mentioned, the endoscope 1 has an operating handle 2 at the proximal end thereof i.e. at the left-hand side of FIG. 1*a*. The operating handle 2 is assembled from and comprises a number of handle parts to be described later. From the operating handle 1, the insertion tube 3 comprising a number of insertion tube parts to be described later extends towards the distal end of the endoscope, i.e. towards the right-hand side of FIG. 1*b*.

The operating handle 2 comprises at least two shell parts 9, 10 forming the outer housing walls of the handle housing of the operating handle 2. The two shell parts 9, 10 form the outer housing walls and are shaped to provide an ergonomically suitable operating handle for an operator, gripping it with one hand. In addition to the two shell parts 9, 10 a transition part 11 forming the transition from the operating handle to the insertion tube 3, may be provided. This transition part may also form part of the handle housing. However, the two shell parts 9, 10 constitute the major part of the housing in the embodiment shown. The shell parts 9, 10 and almost all other parts are mounted on a chassis 12.

As best seen in FIG. 5, the chassis 12 preferably shell shaped, i.e. the chassis 12 comprises an essentially shell shaped structure with a shell wall having an inner surface 16 and an outer surface 17 linked by an edge 18, said essentially shell shaped structure defining an interior compartment 19 delimited by said inner surface 16 and the edge 18 of the shell wall, the edge thus defining main opening 20 of said interior compartment 19. It will be understood that the chassis 12 can be designed mainly based on technical requirements, in such as kinematic chains of movable parts to be described further below, and thus be optimized for those technical requirements without having to inherit constraints from the ergonomic requirements of the handle 2, i.e. the shape of the two shell parts 9, 10.

As mentioned above, the chassis 12 is adapted for the mounting of almost all parts of the endoscope 1. In particular, the chassis 12 is adapted for holding movable parts forming of kinematic chain from the push-button forming the tool operating member to the motion transfer means transferring the movement of the tool operating member 22 to the tool 55.

One such adaptation is a pair of apertures 41 in the form of essentially cylindrical through holes which can be seen in FIG. 1*a*. The apertures 41 serve as bearings of trunnions 42 carrying rotary member such as a pinion 44, best visible in FIG. 9. As can be seen from FIGS. 12 to 14, the pinion 44 is adapted to be in engagement with a curved rack 45. The curved rack 45 is shown separately in FIG. 10. The curved rack 45 has a first free end 46 and a second end with trunnions 47 held loosely in suitable receptacles inside the push button forming the tool operating member 22. The rack 45 as such is loosely held in a guideway comprising a first side 85, a second side 86 and a curved bottom 87 adapted to keep the rack 45 in engagement with the pinion 44. The first side 85 and the second side 86 as well as the curved bottom 87 are preferably formed integrally with the remainder of the chassis 12, e.g. in an injection moulding process. The first side is preferably constituted by a plane surface of a thickened part of the wall, i.e. a raised part of the inner surface 16 of the chassis 12.

Rotation of the pinion 44 may be effected by an operator moving the push-button forming the tool operating member 22, e.g. depressing it using an index finger, upon which the push-button forming the tool operating member 22 transfer motion to the curved rack 45, in turn rotating the pinion 44.

On the pinion 44, two levers 48 and 49 are provided. These levers 48 and 49 are in rigid connection with the pinion 44. The levers 48 and 49 have different lengths so as to influence a first motion transfer member 53 and a second transfer member 54 of the motion transfer means in different ways in order to effect a compound movement of the tool 55. As will be described later this compound movement comprises both a linear movement of the tool 55 and a task movement of the tool 55.

As can best be seen in FIG. 1*a*, the first motion transfer member 53 is arranged co-axially within the second motion transfer member 54. The first motion transfer member 53 and the second motion transfer member 54, in turn, are arranged within in tubular members 71, 72, 73, 74, which form part of the working channel of the endoscope, together with an e.g. T- or Y-shaped bifurcated section 75 providing the entry port to the working channel.

As can best be seen from FIGS. 15*a*-15*c* the first and second motion transfer members 53, 54 each comprise different sectors with different rigidities or bending properties, matching the requirements of the insertion tube 3, and the working channel, which both also has different bending properties along the length thereof. The first motion transfer member 53 preferably comprises a rigid rod piece at the proximal end and a rod or tubular piece at the tool 55. Between the two, the first motion transfer means may comprise a flexible wire.

The first motion transfer member 53 is terminated in an end sealing means 51. Apart from sealing the proximal end of the working channel, the end sealing means also serves as part of a first kinematic chain by being pivotally connected to the first lever 48.

The first kinematic chain is as follows: Depressing the tool operating member 22 will move the rack 45 in a curvilinear movement via the trunnions 47. The rack 45, which has teeth in permanent engagement with the pinion 44, will rotate the pinion 44 and the first lever 48 rigidly connected thereto. The rotating first lever will consequently push the proximal end of the first motion transfer member 53, causing the tool 55 arranged at distal end of the first motion transfer member 31 to be moved out of the working channel beyond the distal end of the insertion tube 3 of the endoscope 1. Being spring biased, by e.g. a pair of coil springs 83 accommodated in the chassis 12, a release of the tool operating member 22 will automatically return the tool operating member 22 to the position of FIG. 4*a*.

The second motion transfer member 54 forms a sheath for the first motion transfer member and preferably comprises a coil spring part 54*a* wound from wire with a rectangular cross section towards the proximal end, and a coil spring part 54b wound from wire with a circular or round cross section towards the distal end. At the distal end, the second motion transfer member is terminated in a rigid tubular member 95.

The second motion transfer member 54 is terminated in a first tubular end member 52. The rigid part of the first motion transfer member 53 passes coaxially trough the first tubular end member 52 and into the remainder of the second motion transfer member 54. The passage through the first tubular end member 52 as well as through the remainder of the second motion transfer member 54 is adapted to allow mutual lengthwise relative motion, i.e. mutually reciprocating movement.

Not unlike the sealing end member 51, the first tubular end member 52 serves as part of a second kinematic chain adapted to provide a different motion pattern of the second motion transfer member 54 as compared to the first motion transfer member 53 in response to the very same depression, i.e. one and the same as the one described above. This is achieved by the second lever 49 which is also rigidly attached to the pinion 44 but has a different length than the first lever 48. At the end of the second lever 49 a first arm 50 is provided in articulated connection with said second lever 49. The second end of the first arm 50 is in articulated connection with a clamping means 79 adapted to clamp the tubular end means 52 with a part 71 of the working channel wall interposed. The interposed part 71 is preferably a flexible hose part. Preferably, the flexible hose part is made from the very same tubular material as is used to form the outer sheath 80 of the insertion tube 3 at the distal end around the bending portion 5. To ensure good grip between the interposed part of the working channel wall 71 and the first tubular end member 52 the first tubular end member may comprise concentric ribs 98 or corrugations, or similar means. The articulations of the first arm 50 are preferably provided as integrally moulded foil hinges 93, as best seen in FIG. 12.

Accordingly, the second kinematic chain is as follows: Depressing the tool operating member 22 will move the rack 45 in a curvilinear movement via the tool trunnions 47. The rack 45, which has teeth in permanent engagement with the pinion 44, will rotate the pinion 44 and the second lever 49 rigidly connected thereto, so as to change their relative position while remaining in the engagement. The rotating second lever 49 will consequently push the proximal end of the first arm 50, thereby moving clamping means 79 at distal end of the first arm 50, articulating the first arm 50 as necessary in the foil hinges 93. The clamping means 79 moves the clamped part of the working channel wall part 71. Being clamped, the clamped part of the working channel wall 71 moves the first tubular end member of the second motion transfer member 54 towards the distal end of the working channel, consequently causing the distal end of the second motion transfer member 54 to be moved out of the working channel beyond the distal end of the insertion tube 3 of the endoscope 1. The distal end of the second motion transfer member 54 is preferably terminated in a second tubular end member 95. Being spring biased, by e.g. a pair coil springs 83 accommodated in the chassis 12, a release of the tool operating member 22 will automatically return the tool operating member 22 to the position of FIG. 4a.

Providing these two different kinematic chains allows the tool 55 to perform a compound movement comprising both a linear movement and a task movement, during one continuous depression of the tool operating member 22. In the linear movement, the tool 55 is advanced to a position in front of the distal end of the insertion tube 3 of endoscope 1 where it is visible from the camera built into the tip part 4 of the endoscope 1, and hence visible by the operator on the monitor 92 attached to the endoscope via cable 7 and connector. This may be performed by only partially depressing the tool operating member 22, e.g. to the position shown in FIG. 2, where with a suitable layout of the first kinematic chain will not advance any further but remain stationary or at least almost stationary with respect to the distal end of the insertion tube 3 of the endoscope even if the tool operating member is depressed further. Having located the correct position for operating the tool 55, e.g. by laterally moving the tip 4 of the bending section 5 at the distal end of the insertion tube 3 of the endoscope 1 using the first operating member 6 simultaneously with the tool operating member, the task movement can be performed.

In the preferred embodiment the tool 55 at the distal end of the first motion transfer member 53 comprises a self expanding configuration, such as a pair of spring tweezers, forceps, a spring loop, or the like which as long as it is accommodated in the tubular member 95 is compressed, as shown in FIG. 15b. Accordingly, it will auto-expand if it is advanced out the second tubular member 95, to the configuration shown in FIG. 2. Now, due to the second kinematic chain operating independently of the first kinematic chain, the second motion transfer member is held stationary is in the working channel during the first part of the depression of the tool operating means 22 to the intermediate position. Then, still due to the independent operation of the first and second kinematic chains, continuing the continuous movement by further depressing of the tool operating member 22 will cause the second motion transfer member to also start moving thereby advancing the second tubular end member 95. Consequently, the second tubular end member 95 slides over the tool 55 again, because as mentioned above the first kinematic chain is laid out to keep the tool 55 stationary in the field of vision of the camera at a distance from the tip part 4 of the insertion tube 3 of the endoscope 1. This will the effect the task movement of closing the tool 55 because the configuration as show in FIG. 15b is now restored, but this time at the position at the location outside the working channel set at the intermediate depression of the tool operating member 22. Keeping this position is of outmost benefit for the operator, who having only one camera eye does not perspective vision and therefore as difficulties in judging distances. Thus, having found the position where a stent a other object is to be gripped, e.g. by touching them with the tool, the operator can do so without further advancing or retracting of the entire endoscope 1.

Having gripped object, such as a stent, with the tool 55 in this way the object may then be removed from the body by retracting the entire endoscope 1 from the cavity whilst holding the tool operating member 22 depressed.

For the sake of clarity it should be noted that the term continuous movement is merely to be understood as a movement of the tool operating member from released state to a depressed state. It does not imply that the movement cannot be paused by the operator during the continuous movement. It does also not imply that the movement cannot be partially reversed by the operator releasing the tool operating member 22, in the search for the gripping location. In fact a latch means may be included to partially intermit the procedure without the tool changing its position. This could be a simple click mechanism as is well known in the art, latching when the tool operating member 22 is depressed fully, and releasing upon repeated depression of the tool operating member 22. As mentioned above, and as can be seen from FIGS. 10 and 12-14 the rack 45 has a curvature. This curvature preferably matches the curvature of the curved bottom 87 of the guideway, so that the teeth of the rack 45 are kept in engagement with the matching teeth of the pinion 44. This curvature saves space helping to fit the rack 45 and pinion 44 mechanism within the chassis 12 and the handle housing 2. The skilled person will understand that the forces and torques of the kinematic chain may be also be influenced by suitable choice of curvature and length of the rack 45 and diameter of the pinion 44 provided it is generally circular. The pinion 44 with a generally oval shape or other curvature is also envisaged. The skilled person will also understand that the two kinematic chains, and in particular their mutual differences could be influenced by suitable choice of the length of the levers 48 and 49, their angular spacing on the pinion 44, and the length and articulations of the arm 50, as well as by the provision of further arms. This may allow specific adaptation of the kinematic chains to the specific requirements of different tools 55.

As will be understood from the above the first and second motion transfer members are located within the working channel of the endoscope 1, comprising tubular members 71, 72, 73, 74 forming a generally tubular working channel wall and an e.g. T- or Y-shaped bifurcated section 75 providing the entry port to the working channel.

Starting from the distal end of the endoscope 1, a first tubular member 72 adapted to comply with the bending requirements of the bending section 5 of the endoscope 1 is provided. The first tubular member 72 passes through the bending section and thus provides an exit port 96 of the working channel at the tip 4 thereof. Via a short joint tube 74, a second tubular member 73 is joined at one end with the first tubular member 72 and provides a longer intermediate section of the working channel. The second tubular member 73 is generally more rigid than the first tubular member 72. The second tubular member 73 is however still quite flexible. More specifically, the second tubular member 73 and a second outer tube section 81 surrounding it are so flexible that they allow a loose knot to be tied on the insertion tube 3. The alternative is a rigid or semi-rigid endoscope where the insertion portion is rigid, only slightly bendable or hinged, and which does not allow a knot to be tied on the insertion tube. It is preferred to make the first tubular member 71 of a first polyurethane elastomer and to make the first tubular member 72 of another polyurethane elastomer. Both polyurethane elastomers could be Pellethane®, which is available in different variants. The second tube member 73 may also comprise polyurethane. At the other end of the second tubular member 73, the second tubular member 73 is joined to a first branch of a preferably T-shaped bifurcated section 75. The bifurcated section has s second branch which provides the entry port to the working channel together with a connector 76 or lead-in mounted on the chassis 12. In the preferred embodiment shown the bifurcated section is 75 T-shaped. That is to say perpendicular that the second branch is perpendicular to the first branch. Evidently the second branch could also be arranged a different angle, so as to provide more of a Y-shape. The connector 76 allows a suction means to be attached for extracting fluid from a body cavity via the working channel. Alternatively a fluid source may be attached to the connector 76, allowing e.g. irrigation or aspiration of the body cavity via the working channel. The third branch of the bifurcated section 75 is preferably aligned with the first branch so as to provide an unobstructed straight passage through the bifurcated section 75 for the first and second motion transfer members 53, 54. To the third branch of the bifurcated section a first end of a third tubular member is attached, which at least in the released position of the operating member 22 is aligned with the first and third branch of the bifurcated section 75 and the second tubular member 73, when the latter is in a relaxed position, i.e. not influenced by external forces from body cavity walls or the like. The second end of the third tubular member 71 forms the proximal end of the working channel, and is terminated in an end sealing means 51. As described above end sealing means, not only seals the proximal end of the working channel, but also serves as part a first kinematic chain by being pivotally connected to the first lever 48. The third tubular member 71 is preferably in the form of a hose of a highly flexible material, as compared to the remainder of the tubular members forming the working channel. The hose could be provided with corrugations or the like to from a bellows. Making the third tubular member of a highly flexible material serves two purposes.

The first purpose is that it allows the length of the working channel to adapt to the movement of the members of the first kinematic chain in particular the first lever 48, the first motion transfer member 53 and the interposed end sealing member 51. The flexible material allows the working channel to deform in order to adapt in length to accommodate the movement of the first motion transfer member. However, by being flexible the material also allows working channel to deform in order to comply with the swinging movement of the end sealing member caused by the first lever 48 moving the end sealing member 51 out of alignment with the first and third branches of the bifurcated member 75 and second tubular member 73. By being able to comply with these movements, the third tubular member 71 allows transfer of movement using parts of the working cannel itself, in turn, allowing transfer of movement from the operating means 22 to the tool 55 without breaching the integrity of working channel wall. Undesired ingress of pollutants is thus avoided.

The second purpose is similar to the first purpose, because by being flexible the material also allows working channel to deform in order to comply with the movement of the members of the second kinematic chain, in particular the movement of the first tubular end member 52 caused by the second lever 49 in conjunction with the arm first 50. As mentioned above this movement is transferred via the working channel wall, because the third tubular member 72 is clamped between the first tubular end member 52 and clamping member 79. By being able to comply with these movements, the third tubular member 71 allows transfer of movement using parts of the working cannel itself, in turn, allowing transfer of movement from the operating means 22 to the tool 55 without breaching the integrity of working channel wall. Undesired ingress of pollutants is thus avoided.

Clamping the third tubular member 72 in this way between the clamping member 79 and first tubular end member 52, provide minor problems which the present invention also overcomes. One problem is to ensure good grip so that the relative position between the clamping member 79 and the first tubular end member 52 does not change due to the forces in the kinematic chain when the tool 55 is operated. The first tubular end member 52 the first tubular end member may comprise concentric ribs 98 or corrugations, or similar means. A second problem is with this configuration of the working channel with a sealed appendix at the proximal end, the output port at the distal end, and entry port located between them, it becomes difficult to sterilize the interior of the appendix, in particular the proximal end thereof between the end sealing means 51 and the first tubular end member 52, because the access of sterilizing fluid, such as Ethylene Oxide, may be blocked by the first tubular end member 52. Sterilisation with Ethylene Oxide (ETO sterilization) is preferred for sterilisation, because the endoscope 1 according to the invention is preferably a disposable endoscope made from low cost materials, which may not necessarily withstand other sterilization processes such as the high temperature and pressure of an autoclave sterilisation.

Accordingly, as can be seen in FIG. 15a an elongate groove along the first tubular end member 52 and across the concentric ribs 98 is provided. In assembly this groove is made to register with gap in the clamping means 79, so as to allow an open fluid passage along the first tubular end member 52. Preferably, the inner diameter of the third tubular member 71 is selected to be larger than the largest outer diameter of the first tubular end member 52 so as to form a pouch in the first tubular member 71 also registering with the groove 99.

A third problem is that using the working channel wall as a part of the kinematic chains, and therefore in the second kinematic chain gripping and the third tubular member 71 somewhere between the sealing end member 51 and the bifurcated section 75, may cause inadvertent overstretching of the flexible material of the third tubular member, leading, in turn, to an undesired rupture of the working channel wall. To overcome this, a strike plate 59 is provided in the chassis 12. When the clamping member 79 is moved under the by depression of the operating member 22 by the operator, the clamping member will strike the underside (as understood with reference to FIG. 1) of the strike plate 59, and will be limited in further motion. Thus even if the operator presses inappropriately hard on the operating member 22, the clamping means will not tear the third tubular member 71 and breach the integrity of the working channel wall. Preferably, the strike plate serves the dual purpose of also accommodating electronics of the endoscope 1 such as a printed circuit board 62.

The present invention thus provides an endoscope with a working channel, used not only for accommodating parts of the control mechanism of a tool but also forming itself a part of the control mechanism. The skilled person will understand that the arrangements described above, and in particular the kinematic chains are only exemplary embodiments, and that the endoscope according to the present invention may be devised in many different variants without departing from the scope of the invention as expressed in the claims.

What is claimed is:

1. An endoscope comprising:
   a handle including a handle housing having a proximal end and a distal end opposite the proximal end;
   a tool actuator;
   an insertion tube extending from the distal end of the handle housing and terminating in a tip part;
   a working channel having a proximal end in the handle housing and an exit port at the tip part, the working channel extending from the proximal end to the exit port;
   a tool at the tip part;
   a motion transfer linkage within the working channel and connected to the tool; and
   an end connector sized and shaped to seal the proximal end of the working channel and operably connecting the tool actuator with the motion transfer linkage.

2. The endoscope of claim 1, wherein the motion transfer linkage is rigidly attached to the end connector.

3. The endoscope of claim 1, further comprising a motion transfer sheath, wherein the motion transfer linkage is positioned within the motion transfer sheath, and wherein the motion transfer linkage and the motion transfer sheath are operable to translate within the working channel and relative to each other responsive to actuation of the tool actuator.

4. The endoscope of claim 3, further comprising a rack and pinion assembly connected to the tool actuator and including a first lever connected to the motion transfer linkage and a second lever connected to the motion transfer sheath, the first lever and the second lever sized to provide different motion patterns of the motion transfer linkage and the motion transfer sheath.

5. The endoscope of claim 4, wherein the rack and pinion assembly is sized and shaped to convert a continuous movement of the tool actuator into a linear movement of the tool during a first part of the continuous movement and a task movement of the tool during a second part of the continuous movement.

6. The endoscope of claim 5, wherein the first part of the continuous movement advances the motion transfer linkage and the second part of the continuous movement advances the motion transfer sheath.

7. The endoscope of claim 6, wherein the motion transfer sheath remains stationary during the first part of the continuous movement.

8. The endoscope of claim 4, wherein the rack and pinion assembly includes a pinion with a non-circular radial cross-section.

9. The endoscope of claim 4, wherein the rack and pinion assembly includes a pinion, further comprising a chassis sized and shaped to support the pinion within the handle housing.

10. The endoscope of claim 9, wherein the chassis comprises a stop to limit distal movement of the motion transfer linkage.

11. The endoscope of claim 3, further comprising a first kinematic chain between the tool actuator and the motion transfer linkage, the first kinematic chain including the end connector.

12. The endoscope of claim 11, further comprising a second kinematic chain between the tool actuator and motion transfer sheath.

13. The endoscope of claim 12, wherein the second kinematic chain comprises a portion of the working channel that is adjustable in length.

14. The endoscope of claim 13, wherein the portion of the working channel that is adjustable in length is structured to adjust in length responsive to movement of the end connector.

15. The endoscope of claim 14, further comprising an entry port interposed between the proximal end and the exit port.

16. The endoscope of claim 15, wherein the portion of the working channel that is adjustable in length is positioned between the end connector and the entry port.

17. The endoscope of claim 3, wherein the motion transfer sheath comprises two or more sections different from each other in rigidity.

18. The endoscope of claim 17, wherein the two or more sections include a distal rigid tube section which is more rigid than the other of the two or more sections.

19. The endoscope of claim 1, further comprising an entry port interposed between the proximal end and the exit port.

20. The endoscope of claim 19, wherein the working channel comprises a bifurcated section providing the entry port.

21. The endoscope of claim 20, wherein a portion of the working channel is adjustable in length in response to movement of the end connector.

22. The endoscope of claim 21, wherein the portion of the working channel that is adjustable in length is positioned between the end connector and the entry port.

23. The endoscope of claim 22, wherein the portion of the working channel that is adjustable in length is comprised by a hose which is more flexible than the remainder of the working channel.

24. The endoscope of claim 1, further comprising a rack and pinion assembly connected to the tool actuator and including a first lever and a second lever, wherein the end connector comprises a distal end affixed to the motion transfer linkage and sized and shaped to fit in the proximal end of the working channel, and wherein the end connector comprises a proximal end pivotally connected to the first lever.

25. An endoscope comprising:
- a handle including a handle housing having a proximal end and a distal end opposite the proximal end;
- a tool actuator;
- a rack and pinion assembly connected to the tool actuator and including a first lever and a second lever;
- an insertion tube extending from the distal end of the handle housing and terminating in a tip part;
- a working channel having a proximal end in the handle housing and an exit port at the tip part, the working channel extending from the proximal end to the exit port;
- a tool at the tip part;
- a motion transfer sheath connected to the second lever;
- a motion transfer linkage positioned within the motion transfer sheath and connecting the tool actuator to the first lever, the motion transfer linkage operable to translate within the working channel relative to the motion transfer sheath responsive to actuation of the tool actuator, the first lever and the second lever sized and shaped to provide different motion patterns of the motion transfer linkage and the motion transfer sheath.

26. An endoscope comprising:
- a handle including a handle housing having a proximal end and a distal end opposite the proximal end;
- a tool actuator having a depressed position, a released position, and an intermediate position intermediate the depressed position and the released position;
- a pinion rotatable by operation of the tool actuator;
- a first lever and a second lever having different lengths, the first lever and the second lever rigidly connected to the pinion;
- a working channel having a flexible portion;
- a motion transfer linkage connected to the first lever;
- a motion transfer sheath surrounding at least a portion of the motion transfer linkage;
- a first arm connected to the second lever;
- a clamp connected to the first arm and surrounding a portion of the motion transfer sheath with the flexible portion of the working channel therebetween; and
- a tool,
wherein depression of the tool actuator to the intermediate position moves the tool distally, and wherein depression of the tool actuator beyond the intermediate position toward the depressed position moves the motion transfer sheath distally without moving the tool distally.

* * * * *